United States Patent [19]

Brankovan et al.

[11] Patent Number: 5,236,905
[45] Date of Patent: Aug. 17, 1993

[54] IN VITRO METHOD OF INHIBITION OF HIV USING TRANSFORMING GROWTH FACTOR-BETA

[75] Inventors: Vera Brankovan, Seattle; Mario N. Lioubin, Bellevue; Anthony F. Purchio, Seattle, all of Wash.

[73] Assignee: Oncogen, Seattle, Wash.

[21] Appl. No.: 236,698

[22] Filed: Aug. 25, 1988

[51] Int. Cl.⁵ ............................................. A61K 37/36
[52] U.S. Cl. ..................................... 514/12; 514/885; 514/931
[58] Field of Search ........................... 514/12, 885, 931

[56] References Cited

PUBLICATIONS

DS. Kabat, Bioscience, 40, No. 9, 691–692, Oct. 1990.
Ho et al., Lancet, 602, Mar. 16, 1985.
Folks et al., J. Immunol., 136, No. 11, 4049–4053, 1986.
Folks et al., Science, 238, 800–802, 1987.
Folks et al., J. Immunol., 140, No. 4, 1117–1122, 1988.
Clause et al., J. Immunol., 142, 431–438, 1989.
Folks et al., Proc. Natl. Acad. Sci. USA, 86, 2365–2368, 1989.
Poli et al., Science, 244, 575–577, 1989.
Poli et al., J. Exp. Med. 173, 589–597, 1991.
Michael S. McGrath in The Aids Knowledge Base, edited by P. T. Cohen et al., The Medical Publishing Group, Waltham, Mass., Sections 3.2.1–3.2.5, 1990.
Fauci, Science 239: 617–622 (1988).
Roberts and Sporn, Adv. in Cancer Res. 51: 107–145 (1988).
Keski-Oja et al., J. Cell. Biochem. 33: 95–107 (1987).
Wahl et al., Proc. Natl. Acad. Sci. USA 84: 5788–5792 (1987).
Tsunawaki et al., Nature 334: 260–262 (1988).
Shalaby and Ammann, Cell Ummunol. 112: 343–350 (1988).
Kahri et al., J. Exp. Med. 163: 1037–1050 (1986).
Rook et al., J. Immunol. 136: 3916–3920 (1986).
Folks et al., Science 238: 800–802 (1987).
Ho et al., Lancet i: 602–604 (1985).
Wong et al., J. Immunol., 140: 120–124 (1988).
Hammer et al. Proc. Natl. Acad. Sci. USA 83: 8734–8738 (1986).
Hammer et al., Antimicrob. Agents Chemother. 31: 1046–1050 (1987).

Primary Examiner—F. T. Moezie
Attorney, Agent, or Firm—Pennie & Edmonds

[57] ABSTRACT

The use of TGF-$\beta$ to inhibit HIV infection and/or replication is described. Both mature and precursor forms of TGF-$\beta$ are efficacious in inhibiting production of HIV. The TGF-$\beta$ used to inhibit HIV may be obtained from natural sources or may be produced by recombinant DNA or chemical synthetic techniques. TGF-$\beta$1 and/or TGF-$\beta$2 may be used. Additionally, hybrid TGF-$\beta$1/$\beta$2 molecules may also be utilized.

6 Claims, 10 Drawing Sheets

FIG.1A

FIG.1B

```
                         260                                              270
SIMIAN  Ile His Gly Met Asn Arg Pro Phe Leu Leu Leu Met Ala Thr Pro Leu Glu Arg Ala Gln His Leu Gln Ser Ser  823
        ATT CAT GGC ATG AAC CGG CCT TTC CTG CTT CTC ATG GCC ACC CCG CTG GAG AGG GCC CAA CAT CTG CAA AGC TCC
HUMAN   ... ... ... ... ... ... ... ... ... ... ... ... ... ... ... ... ... ... ... ... ..G ... ... ... ...

285                                              295
SIMIAN  Arg His Arg Arg Ala Leu Asp Thr Asn Tyr Cys Phe Ser Ser Thr Glu Lys Asn Cys Cys Val Arg Gln Leu Tyr  897
        CGG CAC CGC CGA GCC CTG GAC ACC AAC TAC TGC TTC AGC TCC ACG GAG AAG AAC TGC TGC GTG CGG CAG CTG TAT
HUMAN   ... ... ... ... ... ... ... ... ... ..T ... ... ... ... ... ... ... ... ... ... ... ... ... ... ..C 310                                              320
SIMIAN  Ile Asp Phe Arg Lys Asp Leu Gly Trp Lys Trp Ile His Glu Pro Lys Gly Tyr His Ala Asn Phe Cys Leu Gly  972
        ATT GAC TTC CGC AAG GAC CTC GGC TGG AAG TGG ATC CAC GAG CCC AAG GGC TAC CAT GCC AAC TTC TGC CTG GGG
HUMAN   ... ... ... ... ... ... ... ... ... ... ... ... ... ... ... ... ... ... ... ... ... ... ... ..C ...

335                                              345
SIMIAN  Pro Cys Pro Tyr Ile Trp Ser Leu Asp Thr Gln Tyr Ser Lys Val Leu Ala Leu Tyr Asn Gln His Asn Pro Gly  1047
        CCC TGT CCC TAC ATT TGG AGC CTG GAC ACG CAG TAC AGC AAG GTC CTG GCC CTG TAC AAC CAG CAT AAC CCG GGC
HUMAN   ... ..C ... ... ... ... ... ... ... ... ... ... ... ... ... ... ... ... ... ... ... ... ... ... ...

360                                              370
SIMIAN  Ala Ser Ala Ala Pro Cys Cys Val Pro Gln Ala Leu Glu Pro Leu Pro Ile Val Tyr Tyr Val Gly Arg Lys Pro  1122
        GCC TCG GCC GCG CCG TGC TGC GTG CCG CAG GCG CTG GAG CCA CTG CCC ATC GTG TAC TAC GTG GGC CGC AAG CCC
HUMAN   ... ... ... ... ... ... ... ... ... ... ... ... ... ..G ... ... ... ... ... ... ... ... ... ... ...

385
SIMIAN  Lys Val Glu Gln Leu Ser Asn Met Ile Val Arg Ser Cys Lys Cys Ser TGA GGCCCCGGCCCCGGCCCCACCCCGGGCAG  1204
        AAG GTG GAG CAG CTG TCC AAC ATG ATC GTG CGC TCC TGC AAA TGC AGC
HUMAN   ... ... ... ... ... ... ... ... ... ... ... ... ... ... ..G ... ...   ......................T..........

SIMIAN  GCCCGGCCCCGCTCTTGCCCTGTCTTGGGGCTGTATTTAAGGACACCCGTGCCCAAGCCACCTGGGGCCCATTAAAGA                       1300
HUMAN   .......A....G........C.......A................................................
```

FIG.1C

```
-467                                                                                                                                           -397
              GCCCCTCCGTCAGTTCGCCAGCTGCCAGCCCGGGACCTTTTCATCTCTCCCTTTGGCCGGAGGAGCC

GAGTTCAGATCGCGCCACTCCGCACCCGAGACTGACACACTGAACTCCACTTCCTCCTCTCTTAAATTTATTCTACTTAATAGCCACTCGTCTCTTTTTT                                          -298

CCCCATCTCATTGCTCCAAGAATTTTTTCTCTTACTCGCCAAAGTCAGGGTCCCTCGCCGTCCGTATTAATATTCCACTTTTGAACTACTG                                                   -199

GCCTTTTCTTTTAAAGGAATTCAAGCAGGATACGTTTTCTGTGGGCATTGACTAGATTGTTGCAAAAGTTCGCATCAAAAACAACAACAACAAA                                                -100

AAACCAAACAACTCTCCTTGATCTATACTTTGAGAATTGTTGATTCTTTTTTATTCTGACTTTTAAAAACAACTTTTTTCCACTTTTTAAAAA                                                   -1
                                                                     20↓
Met His Tyr Cys Val Leu Ser Ala Phe Leu Ile Glu Ala Phe Met Arg Gly Gln Ile Arg Leu Ser Leu Lys Leu                                              75
ATG CAC TAC TGT GTG CTG AGC GCT TTT CTG ATC GAG GCG TTC ATG CGC AAG AGG ATC CGC GGG CAG ATC CGC CTG AGC AAG CTG
                                T                                                                                              45
                              35
Thr Leu Asp Met Asp Gln Phe Met Arg Lys Arg Ile Glu Ala Ile Arg Gly Gln Ile leu Ser Lys Leu Lys Leu
ACA CTC GAT ATG GAC CAG TTC ATG CGC AAG AGG ATC GAG GCG ATC CGC GGG CAG ATC CTG AGC AAG CTG AAG CTC                                             150

60                                    70 *                                  
Thr Ser Pro Pro Glu Asp Tyr Pro Glu Glu Val Pro Pro Glu Val Ile Ser Glu Val Ile Tyr Asn Ser Thr Arg
ACC AGT CCC CCA GAA GAC TAT CCT GAG GAA GTC CCC CCG GAG GTG ATT TCC GAG GTG ATC TAC AAC AGC ACC AGG                                             225

85                                    95
Asp Leu Gln Glu Lys Ala Ser Arg Arg Ala Ala Cys Glu Arg Ser Arg Glu Arg Ser Asp Glu Glu Tyr Tyr Ala
GAC TTG CTC CAG GAG AAG GCG AGC CGG AGG GCC GCC TGC GAG CGC AGC AGG GAG AGG AGC GAC GAA GAG TAC TAC GCC                                         300

110                                   120
Lys Glu Val Tyr Lys Ile Asp Met Pro Pro Phe Phe Pro Ser Glu⌈Thr Val Cys Pro Val Val Thr Thr Pro Ser
AAG GAG GTT TAC AAA ATA GAC ATG CCG CCC TTC TTC CCC TCC GAA⌊ACT GTC TGC CCA GTT GTT ACA ACA CCC TCT                                              375
```

FIG.2A

```
                                                        135
Gly Ser Val Gly Ser Leu Cys Ser Arg Gln Ser Gln Val Leu Cys Gly Tyr Leu Asp  Ala Ile Pro Pro Thr Phe
GGC TCA GTG GGC AGC TTG TGC TCC AGA CAG TCC CAG GTG CTC TGT GGG TAC CTT GAT  GCC ATC CCG CCC ACT TTC  450
                                                                        145

160                                                      170
Tyr Arg Pro Thr Phe Arg Ile Val Arg Phe Asp Val Ser Ala Met Glu Lys Asn Ala Ser Asn Leu Val Lys Ala
TAC AGA CCC ACC TTC AGA ATT GTT CGA TTT GAC GTC TCA GCA ATG GAG AAG AAT GCT TCC AAT TTG GTG AAA GCA  525
                                    G          *

185                                                      195
Glu Phe Agt Val Phe Arg Leu Gln Asn Pro Lys Ala Arg Val Pro Glu Gln Arg Ile Glu Leu Tyr Gln Ile Leu
GAG TTC AGA GTC TTT CGT TTG CAG AAC CCA AAA GCC AGA GTG CCT GAA CAA CGG ATT GAG CTA TAT CAG ATT CTC  600
                                                                                     G 210                                                      220
Lys Ser Lys Asp Leu Thr Ser Pro Thr Gln Arg Tyr Ile Asp Ser Lys Val Val Lys Thr Arg Ala Glu Gly Glu
AAG TCC AAA GAT TTA ACA TCT CCA ACC CAG CGC TAC ATC GAC AGC AAA GTT GTG AAA ACA AGA GCA GAA GGC GAA  675
                C 235                                                      245
Trp Leu Ser Phe Asp Val Thr His Glu Trp Leu His Lys Asp Arg Asn Leu Gly Phe Lys Ile
TGG CTC TCC TTC GAT GTA ACT CAT GAA TGG CTT CAC CAT AAA GAC AGG AAC CTG GGA TTT AAA ATA  750

260                                                      270
Ser Leu His Cys Pro Cys Cys Thr Phe Val Pro Ser Asn Asn Tyr Ile Ile Pro Asn Lys Ser Glu Glu Leu Glu
AGC TTA CAC TGT CCC TGC TGC ACT TTT GTA CCA TCT AAT AAT TAC ATC ATC CCA AAT AAG AGT GAA GAA CTA GAA  825
                                                                      *                         T 285                                                      295
Ala Arg Phe Ala Gly Ile Asp Gly Thr Ser Thr Tyr Thr Ser Gly Asp Gln Lys Thr Ile Lys Ser Thr Arg Lys
GCA AGA TTT GCA GGT ATT GAT GGC ACC TCC ACA TAT ACT AGT GGT GAT CAG AAA ACT ATA AAG TCC ACT AGG AAA  900
                                                                                  T

FIG.2B
```

```
                                                 310                                                                                                  320
Lys Asn Ser Gly Lys Thr Pro His Leu Leu Leu Met Leu Pro Ser Tyr Arg Leu Glu Ser Gln Gln Thr Asn
AAA AAC AGT GGG AAG ACC CCA CAT CTC CTG CTA ATG TTA CCC TCC TAC AGA CTT GAG TCA CAA CAG ACC AAC         975

335                                                                           345
Arg Arg Lys Lys Arg Ala Leu Asp Ala Ala Tyr Cys Phe Arg Asn Val Gln Asp Asn Cys Cys Leu Arg Pro Leu
CGG CGG AAG AAG CGT GCT GCT TTG GAT GCG GCC TAT TGC TTT AGA AAT GTG CAG GAT AAT TGC TGC CTA CGT CCA CTT    1050
                                                                                                                                        G 360                                                                                     370
Tyr Ile Asp Phe Lys Arg Asp Leu Gly Trp Lys Trp Ile His Glu Pro Lys Gly Tyr Asn Ala Asn Phe Cys Ala
TAC ATT GAT TTC AAG AGG GAT CTA GGG TGG AAA TGG ATA CAC GAA CCC AAA GGG TAC AAT GCC AAC TTC TGT GCT    1125
                                                                                                          A 385                                                                                  395
Gly Ala Cys Pro Tyr Leu Trp Ser Ser Asp Thr Gln His Ser Arg Val Leu Ser Leu Tyr Asn Thr Ile Asn Pro
GGA GCA TGC CCG TAT TTA TGG AGT TCA GAC ACT CAG CAC AGC AGG GTC CTG AGC TTA TAT AAT ACC ATA AAT CCA    1200
                                                                           C 410                                                                                       420
Glu Ala Ser Ala Ser Pro Cys Cys Val Ser Gln Asp Leu Glu Pro Leu Thr Ile Leu Tyr Tyr Ile Gly Lys Thr
GAA GCA TCT GCT TCT CCT TGC TGC GTG TCC CAA GAT TTA GAA CCT CTA ACC ATT CTC TAC TAC ATT GGC AAA ACA    1275

435                                                    442
Pro Lys Ile Glu Gln Leu Ser Asn Met Ile Val Lys Ser Cys Lys Cys Ser ***
CCC AAG ATT GAA CAG CTT TCT AAT ATG ATT GTA AAG TCT TGC AAA TGC AGC TAA AATTCTTGGAAAAGTGGCAAGACCAAA    1356
```

FIG.2C

```
ATGACAATGATGATGATGATGACGACGACAACGATGATGCTTGTAACAAGAAAACATAAGAGAGCCTTGGTTCATCAGTGTTAAAAAATTTT    1456

GAAAAGGCGGTACTAGTTCAGACACTTTGGAAGTTTGTGTTCTGTTGTTAAAACTGGCATCTGACACAAAAAAAAGTTGAAGGCCTTATTCTACATTTC    1556

ACCTACTTTGTAAGTGAGAGAGAGACAAGAAGAGCAAATTTTTTTAAAGAAAAAATAAACACTGGAAGAATTTATTAGTGTTAATTATGTGAACAAGACA    1656

ACAACAACAACAACAACAGGAAAATCCCATTAAGTGTGGAGTTGCTGTACGTCCTATCCCGCCCTCACTTGATTTTTCTGTATTGCTATG    1756

CAATAGGCACCCTTCCATTCTTACTCTTAGAGTTAACAGTGAGTTATTTATTGTGTGTTACTATATAATGAACGTTTCATTGCCCTTGGAAAATAAAA    1856

CAGGTGTATAAAGTGGGAGACCAAATACTTTGCCAGAAACTCATGGATGGCTTAAGGAACTTGAACTCAAACGAGCCAGAAAAAAGAGGTCATATTAAT    1956

GGGATGAAAACCCAAGTGAGTTATTATATGACCGAGAGAAGTCTGCATTAAGATAAAGACCCTGAAAACACATGTTATGTATCAGCTGCCTAAGGAAGCT    2056

TCTTGTAAGGTCCAAAAACTAAAAAGACTGTTAATAAAAGAAACTTTCAGTCAG (POLY A)    2111
```

FIG.2D

```
-261  AGGGATCTGTGGCAGGTCGGAGA---AAGATC----CGTCTCCTGGTACCAGATCTCGCCATCTAGGTT  -198

ATTTCCGTGGGATACTGAGAGACACCCCGGTCCAAGCCTCCCCTCCACCACTGCCGCCCTTCTCCCTGAGGA-CCTCAACTTTCCCTCGAGGCCCTCCTAC  -100

CTTTTCCCGGGGACCCCAGCCCTGCAGGGGCGGGGCCTCCCCACCAAACTAGCCTGTTCGCGCTCTCGGCAGTGCCGGGGGCGCCGCCTCCCCC  -1

Met Pro Pro Ser Gly Leu Arg Leu Leu Leu Pro Leu Leu Leu Trp Leu Leu Val Leu Thr Pro Ser Arg
         ATG CCG CCC TCC GGG CTG CGG CTG CTG CCG CTG CTA CTG CTG TGG CTA CTG GTG CTG ACG CCT AGC CGG   75
                                              10                              20

Pro Ala Ala Gly Leu Ser Thr Cys Lys Thr Ile Asp Met Glu Leu Val Lys Arg Lys Arg Ile glu Thr Ile Arg
CCG GCC GCA GGA CTA TCC ACC TGC AAG ACT ATC GAC ATG GAG CTG GTG AAG CGG AAC CGC ATC GAG ACC ATC CGC  150
                    35                              45

Gly Gln Ile Leu Ser Lys Leu Arg Leu Ala Ser Pro Pro Ser Gln Gly Glu Val Pro Pro Gly Pro Leu Pro Glu
GGC CAG ATC CTG TCC AAG CTG CGG CTC GCC AGC CCC AGC CAG GGG GAG GTG CCG CCC GGG CCC CTG CCC GAG  225
                    60                              70

Ala Val Leu Ala Leu Tyr Asn Ser Thr Arg Asp Arg Val Ala Gly Glu Ser Ala Glu Pro Glu Pro Glu Pro Glu
GCC GTG CTC GCC CTG TAC AAC AGC ACC CGC GAC CGG GTG GCC GGG GAG AGT GCT CCG GAG CCC GAG CCG GAG  300
                    85                              95

Ala Asp Tyr Tyr Ala Lys Glu Val Thr Arg Val Leu Met Val Glu Thr His Asn Glu Ile Tyr Asp Lys Phe Lys
GCC GAC TAC TAC GCC AAG GAG GTC ACC CGC GTG CTA ATG GTG GAA ACC CAC AAC GAA ATC TAT GAC AAG TTC AAG  375
                    110                             120

Gln Ser Thr His Ser Ile Tyr Met Phe Phe Asn Thr Ser Glu Leu Arg Glu Ala Val Pro Glu Pro Val Leu Leu
CAG AGC ACA CAC AGC ATA TAT ATG TTC TTC AAC ACA TCA GAG CTC CGA GAA GCA GTA CCT GAA CCT GTG TTG CTC  450
                    135                             145
```

FIG. 3A

```
                                    160
            Ser Arg Ala Glu Leu Arg Leu Leu Arg Leu Lys Leu Lys Val Glu Gln His Val Glu Leu Tyr Gln Lys Tyr
            TCC CGG GCA GAG CTG CGT CTG CTG AGG CTC AAG CTC AAA GTG GAG CAG CAT GTG GAG CTG TAC CAG AAA TAC    522

195
            Ser Asn Asn Ser Trp Arg Tyr Leu Ser Asn Arg Leu Ala Pro Ser Asn ser Pro Glu Trp Leu Ser Phe Asp
            AGC AAC AAT TCC TGG CGA TAC CTC AGC AAC CGG CTG CTG GCG CCC AGC AAC TCG CCG GAG TGG TTG TCT TTT GAT    597

220
            Val Thr Gly Val Val Arg Gln Trp Leu Ser Arg Gly Gly Glu Ile Glu Gly Phe Arg Leu Ser Ala His Cys Ser
            GTC ACC GGA GTT GTG CGG CAG TGG TTG AGC CGG GGA GGG GAA ATT GAG GGC TTT CGC CTT AGC GCC CAC TGC TCC    672

245
            Cys Asp Ser Lys Asp Asn Thr Leu Gln Val Asp Ile Asn Gly Phe Thr Thr Gly Arg Arg Gly Asp Leu Ala Thr
            TGT GAC AGC AAA GAT AAC ACA CTG CAA GTG GAC ATC AAC GGC TTC ACT ACC GGC CGC CGA GGT GAC CTG GCC ACA    747

270
            Ile His Gly Met Asn Arg Pro Phe Leu Leu Met His Thr Pro Leu Glu Arg Ala Gln His Leu Gln Ser Ser
            ATT CAT GGC ATG AAC CGG CCT TTC CTG CTC ATG CAC ACC CCA CTG GAG AGG GCC CAA CAT CTG CAA AGC TCC    822

295
            Arg His Arg Arg|Ala Leu Asp Ala Ala Tyr Cys Phe Arg Asn Val Gln Asp Asn Cys Cys Leu Arg Pro Leu
            CGG CAC CGC CGA|GCT TTG GAT GCT GCC TAT TGC TTT AGA AAT GTG CAG GAT AAT TGC TGC CTA CGT CCA CTT    894
                                                                                                       G
                                            310                                         320
            Tyr Ile Asp Phe Lys Arg Asp Leu Gly Trp Lys Trp Ile His Glu Pro Lys Gly Tyr Asn Ala Asn Phe Cys Ala
            TAC ATT GAT TTC AAG AGG GAT CTA GGC TGG AAA TGG ATA CAC GAA CCC AAA GGG TAC AAT GCC AAC TTC TGT GCT    969
                                                                                    A
```

FIG.3B

```
                                                                              345
Gly Ala Cys Pro Tyr Leu Trp Ser Ser Asp Thr Gln His Ser Arg Val Leu Ser Leu Tyr Asn Thr Ile Asn Pro
GGA GCA TGC CCG TAT TTA TGG AGT TCA GAC ACT CAG CAC AGC AGG GTC CTG AGC TTA TAT AAT ACC ATA AAT CCA      1044
                                 360                                                  370
Glu Ala Ser Ala Ser Pro Cys Cys Val Ser Gln Asp Leu Glu Pro Leu Thr Thr Ile Leu Tyr Tyr Ile Gly Lys Thr
GAA GCA TCT GCT TCT CCT TGC TGC GTG TCC CAA GAT TTA GAA CCT CTA ACC ATT CTC TAC TAC ATT GGC AAA ACA      1119
                                     C
                             385                               390
Pro Lys Ile Glu Gln Leu Ser Asn Met Ile Val Lys Ser Cys Lys Cys Ser ***
CCC AAG ATT GAA CAG CTT TCT AAT ATG ATT GTA AAG TCT TGC AAA TGC AGC TAA  AATTCTTGGAAAAGTGGCAAGACCAAA     1200
ATGACAATGATGATGATAATGATGATGACGACAACGATGATGCTTGTAACAAGAGAACATAAGAGAGCCTTGGTTCATCAGTGTTAAAAAATTTT         1299
GAAAAGGCGGTACTAGTTCAGACACTTTGGAAGTTTGTGTCTGTTTGTTAAAGAAAAAATAAACACTGGAAGAATTTATTAGTGTTAATTATGTGAACAACGACA 1398
ACCTACTTTGTAAGTGAGAGAGACAAGAAGCAAAATCCCATTAAGTGGAGTTGCTGTACGGTTCCTATCCCGGCCTCACTTGATTTTCTGTATTGCTATG    1497
ACAACAACAACAACAACAGGAAAATCCCATTCTTACTCTTAGAGTTAACAGTGAGTTATTTATTGTGTTACTATATAATGAACGTTTCATTGCCCTTGGAAAATAAAA 1596
CAATAGGCACCCTTCCCATTCTTACTCTTAGAGTTAACAGTGAGTTATTTATTGTGTTACTATATAATGAACGTTTCATTGCCCTTGGAAAATAAAA      1695
CAGGTGTATAAAGTGGAGACAAATACTTTGCCAGAAACTCATGGATGGCTTAAGGAACTTGAACTCAAACGAGCCAGAAAAAAGAGGTCATATTAAT      1794
GGGATGAAAAACCCAAGTGAGTTATTATATGACCGAGAAGTCTGCATTAAGATAAAGACCCTGAAAAACAGATGTTATGTATCAGCTGCCTAAGGAAGCT   1893

TCTTCTAAGGTCCAAAAACTAAAAGAAGACTGTTAATAAAAGAAACTTTCAGTCAG ( POLY A)
```

FIG.3C

IN VITRO METHOD OF INHIBITION OF HIV USING TRANSFORMING GROWTH FACTOR-BETA

1. INTRODUCTION

The present invention is directed to the use of transforming growth factor-beta (TGF-$\beta$) for inhibiting human immunodeficiency virus (HIV) infection or replication. The method of the invention includes the use of TGF-$\beta$1, TGF-$\beta$2, mature forms of such molecules, precursor forms of such molecules as well as hybrids and analogs thereof for inhibiting HIV. The method of the invention is demonstrated by way of examples in which the efficacy of such compounds is measured in an in vitro assay system.

2. BACKGROUND OF THE INVENTION

2.1. TRANSFORMING GROWTH FACTOR-BETA

The transforming growth factor (TGF) family of growth modulating peptides consists of two structurally and functionally dissimilar molecules, TGF-$\alpha$ and TGF-$\beta$. Transforming growth factor-Beta (TGF-$\beta$) is a member of a recently described family of polypeptides that regulate cellular differentiation and proliferation. Other members of this family include Mullerian inhibitory substance (Cate et al., 1986, Cell 45:685–698), the inhibins (Mason et al., 1985, Nature 318:659–663) and a protein predicted from a transcript of the decapentaplegic gene complex of Drosphila (Padgett et al., 1987, Nature 325:81–84).

Transforming growth factor-beta (TGF-$\beta$) consists of two identical disulfide linked subunits having molecular weights of 13,000 (Assoian et al.,, 1983, J. Biol. Chem. 258:7155–7160; Frolik et al., 1983, Proc. Natl. Acad. Sci. USA 80:3676–3680; Frolik et al., 1984, J. Biol. Chem. 260:10995–11000). It has been purified from several tissue sources including placenta (Frolik et al., 1983, Nature 325:81–84), blood platelets (Childs et al., 1982, Proc. Natl. Acad. Sci. USA 79:5312–5316; Assoian et al., 1983, J. Biol. Chem. 258:7155–7160), kidney (Roberts et al., 1983, Biochemistry 22:5692–5698), and demineralized bone (Seyedin et al., 1985, Proc. Natl. Acad. Sci. USA 82:119–123). In the presence of 10% serum and epidermal growth factor, TGF-$\beta$ promotes the anchorage independent growth of normal rat kidney fibroblasts (Roberts et al., 1981, Proc. Natl. Acad. Sci. USA 78:5339–5343; Roberts et al., 1982, Nature 295:417–419; Twardzik et al., 1985, J. Cell. Biochem. 28:289–297); in the presence of 10% serum alone, it is able to induce colony formation of AKR-2B fibroblasts (Tucker et al., 1983, Cancer Res. 43:1518–1586). TGF-$\beta$ has also been shown to cause fetal rat muscle mesenchymal cells to differentiate and produce cartilage specific macromolecules (Seyedin et al., 1986, J. Biol. Chem. 261:5693–5695).

In contrast to its effect on cell proliferation, TGF-$\beta$ purified from human platelets as well as a functionally related protein isolated from African green monkey cells (BSC-1) has been shown to inhibit the growth of certain cells in culture (Tucker et al., 1984, Science 226:704–707). TGF-$\beta$ has also been shown to inhibit the growth of several human cancer cell lines (Roberts et al., 1985, Proc. Natl. Acad. Sci. USA 82:119–123). This bifunctional inhibitory/stimulatory effect of TGF-$\beta$ may depend on several factors including cell type and the physiological state of the cells (for review see Sporn et al., 1986, Science 233:532–534).

cDNA clones coding for human (Derynck et al., 1985, Nature 316:701–705), mouse (Derynck et al., 1986, J. Biol. Chem. 261:4377–4379), and simian (Sharples et al., 1987, DNA 6:239–244) TGF-$\beta$ have been isolated. DNA sequence analysis of these clones indicates that TGF-$\beta$ is synthesized as a large precursor polypeptide, the carboxy terminus of which is cleaved to yield the mature TGF-$\beta$ monomer. Strong sequence homology has been found throughout the TGF-$\beta$ precursor protein from all of the above sources.

Very recently a protein isolated from bovine demineralized bone has been identified as being related to TGF-$\beta$ (Seyedin et al., 1987, J. Biol. Chem. 262:1946–1949). The protein has also been isolated from porcine platelets (Cheifetz et al., 1987, Cell 48:409–415), a human prostatic adenocarcinoma cell line, PC-3 (Ikeda et al., 1987, Biochemistry 26:2406–2410), and a human glioblastoma cell line (Wrann et al., 1987, EMBO 6:1633–1636). Partial amino acid sequence of this protein indicated that it was homologous to TGF-$\beta$ and has been termed TGF-$\beta$2. The human (Derynck et al., 1985, Nature 316:701–705), mouse (Derynck et al., 1986, J. Biol. Chem. 261:4377–4379) and simian (Sharples et al., 1987, DNA 6:239–244) TGF-$\beta$ described previously has been termed TGF-$\beta$1.

2.2. HUMAN IMMUNODEFICIENCY VIRUS

Human immunodeficiency virus is a human retrovirus (HIV) believed to be the causative agent of aquired immune deficiency syndrome (AIDS). The HIV virion or virus particle is a sphere that is roughly 1000 angstrom units across. The particle is covered by a lipid bilayer membrane derived from the outer membrane of the infected host cell. Studding the membrane is an envelope glycoprotein which is synthesized as a precursor of 160 Kd and subsequently processed into two glycoproteins: gp41 which spans the lipid bilayer, and gp120 which extends beyond the lipid bilayer. The envelope covers a core made up of proteins designated p24 and p18. The viral RNA is carried in the core, along with several copies of the enzyme, reverse transcriptase, which catalyzes the assembly of viral DNA.

The HIV genome contains three genes that encode the components of retrovirus particles: env (which codes for the envelope proteins), gag (which codes for the core proteins), and pol (which codes for reverse transcriptase). These three genes are flanked by stretches of nucleotides called long terminal repeats (LTRs). The LTRs include sequences that have a role in controlling the expression of viral genes. However, unlike other retroviruses, the genome of HIV includes at least five additional genes, three of which have known regulatory functions, and the expression of which is thought to have an impact on the pathogenic mechanisms exerted by the virus. The tat gene encodes a protein that functions as a potent trans-activator of HIV gene expression, and, therefore, plays an important role in the amplification of virus replication. The trs/art gene also upregulates HIV synthesis by a trans-acting antirepression mechanism. In contrast, the 3'-orf may down regulate virus expression. The sor gene is not absolutely required for virion formation, but is critical to the efficient generation of infectious virions and influences virus transmission in vitro. The R gene encodes an immunogenic protein of an unknown function.

The critical basis for the immunopathogenesis of HIV infection is believed to be the depletion of the helper/inducer subset of T lymphocytes, which express the CD4 antigen, resulting in profound immunosuppression. Viral killing of these immune cells is thought to be a major factor contributing to the crippling effect HIV has on the immune system. The envelope glycoprotein plays an important role in the entry of HIV into CD4 positive host cells. The gp120 portion has been shown to bind directly to the cellular CD4 receptor molecule, thereby producing HIV's tropism for host cells that express the CD4 receptor, e.g., T helper cells (T4 cells), macrophages, etc.

After HIV binds to the CD4 molecule, the virus is internalized and uncoated. Once internalized, the genomic RNA is transcribed into DNA by the enzyme reverse transcriptase. The proviral DNA is then integrated into the host chromosomal DNA and the infection may assume a "dormant" or latent phase. However, once activation occurs, the proviral DNA is transcribed. Translation and post translational processing results in virus assembly and budding of mature virions from the cell surface.

When active replication of virus occurs, the host CD4+ cell is usually killed. However, the precise mechanism by which HIV exerts its cytopathic effect is unknown. A number of mechanisms for the immunopathogenesis and cytopathic effect of HIV infection have been proposed: the accumulation of large amounts of unintegrated viral DNA in the infected cells; massive increase in permeability of the cell membrane when large amounts of virus bud off the cell surface; speculations that HIV may induce terminal differentiation of infected T4 cells, leading to a shortened life span. There is growing evidence that both the CD4 molecule and the virus envelope play a role in cytopathic effect in HIV infected cells by somehow promoting cell fusion. A prominent feature in the cytopathology of HIV infection is the formation of multinucleated syncytia which appear to be induced by the gp120/gp41 envelope proteins. In contrast, HIV-infected macrophages may continue to produce HIV without cytopathic effects for long periods of time and it is believed that the macrophage is a major reservoir for HIV.

To date, there is no cure for AIDS. Vaccine trials are currently underway in an attempt to control the spread of the virus among the population. However, efforts at controlling the course of disease within an infected patient have been directed mainly towards the use of antiviral agents such as AZT (3'-azido-2',3'-dideoxythymidine), which interfere with the viral polymerase activity and, therefore, viral replication. Very recently clinical trials involving the administration of exogenous CD4 will commence. Soluble CD4 has been found to inhibit HIV replication in CD4 cells in vitro where the soluble CD4 competes with CD4-positive cells for binding HIV. It is hoped that binding of exogenous CD4 to HIV in vivo will "neutralize" viral infectivity and/or inhibit cytopathic fusion. However, the clinical results of such treatment remain to be seen.

3. SUMMARY OF THE INVENTION

The use of TGF-$\beta$ to inhibit HIV infection and/or replication is described. Both mature and precursor forms of TGF-$\beta$ are efficacious in inhibiting production of virus and, as a result, decrease syncytia formation. The TGF-$\beta$ used to inhibit HIV may be obtained from natural sources or may be produced by recombinant DNA or chemical synthetic techniques. TGF-$\beta$1 and/or TGF-$\beta$2 may be used. Additionally, hybrid TGF-$\beta$1/$\beta$2 molecules may also be utilized.

The invention is demonstrated by way of examples in which the mature and precursor form of TGF-$\beta$1, and the mature form of TGF-$\beta$2 inhibited HIV production in an in vitro assay in which a CD4-positive T-cell line was infected with HIV. Viral production was assayed by detecting an HIV core protein, p24, in cell supernatants using an immunoassay, whereas syncytia formation was assessed by observation of infected cells. A reduction in both p24 and syncytia formation was observed in infected cells treated with TGF-$\beta$1 or TGF-$\beta$2.

In a second example, both the mature and precursor forms of TGF-$\beta$1 inhibited HIV production in a monocytic cell line. Viral production was assayed by detecting p24 in cell supernatants as described, and by detecting HIV-induced antigen production in infected cells by immunofluorescence. A reduction in both p24 and HIV-induced antigens was detected in infected cells treated with both forms of TGF-$\beta$.

3.1. DEFINITIONS

The following terms as used herein whether in the singular or plural, shall have the meanings designated.

TGF-$\beta$1: Mature transforming growth factor-$\beta$1. Human or simian TGF-$\beta$1 comprises the amino acid sequence substantially as depicted in FIG. 1C from about amino acid residue number 279 to 390.

TGF-$\beta$1 precursor: Transforming growth factor-$\beta$1 precursor and mature sequence with or without the signal sequences. The simian sequence is substantially depicted in sequential order in FIGS. 1A–1C from about amino acid residue number 1 (inclusive of the signal sequence) to about amino acid residue number 390.

TGF-$\beta$1 Truncated precursor: Transforming growth factor-$\beta$1 precursor with or without the signal sequence, minus the mature sequence. The simian sequence is substantially depicted in sequential order in FIGS. 1A–1C from about amino acid residue number 1 (inclusive of the signal sequence) to about amino acid residue number 278.

TGF-$\beta$2: Mature transforming growth factor-$\beta$2. Human or simian TGF-$\beta$2 comprises the amino acid sequence substantially as depicted in FIG. 2C from about amino acid residue number 331 to about amino acid residue number 442.

TGF-$\beta$2 precursor: A family of transforming growth factor-$\beta$2 molecules comprising precursor and mature sequences with or without the signal sequences. Human or simian TGF-$\beta$2 precursors amino acid sequence are substantially depicted in sequential order in FIGS. 2A–2D from about amino acid residue number 1 (inclusive of the signal sequence) to about amino acid residue number 442 (TGF-$\beta$2-442); or from about amino acid residue number 1 (inclusive of the signal sequence) to about amino acid residue number 442 in which the amino acid sequence from amino acid residue number 116 to amino acid residue number 144 is deleted and replaced by a single Asparagine residue resulting in a molecule 414 amino acids in length (TGF-β2-414). TGF-β2 precursors designated TGF-β2-442 or TGF-β2-414 refer to such precursors whether of human or simian origin.

TGF-β2

Truncated

Precursor: Transforming growth factor-β2 precursor with or without the signal sequence, minus the mature sequence. The human and simian sequences are substantially depicted in sequential order in FIGS 2A–2C from about amino acid residue number 1 (inclusive of the signal sequence) to about amino acid residue number 330; or the identical sequence in which a single Asparagine residue is put in place of the 29 amino acid sequence residue numbers 116 to 144 of the TGF-β2-442 sequence.

Hybrid

TGF-β1/TGF-β2 precursor: A novel transforming growth factor-β precursor molecule comprising the amino acid sequence substantially as depicted in sequential order in FIGS. 3A–3C from about amino acid residue number 1 to about amino acid number 390. The TGF-β2 mature coding sequence is joined in-phase (i.e., in the same translational reading frame) to the TGF-β1 signal and precursor sequence.

The non-hybrid TGF-β molecules described above may be obtained from natural sources as described herein or produced by recombinant DNA technology or chemical synthetic methods.

4. DESCRIPTION OF THE FIGURES

Figure 1A:
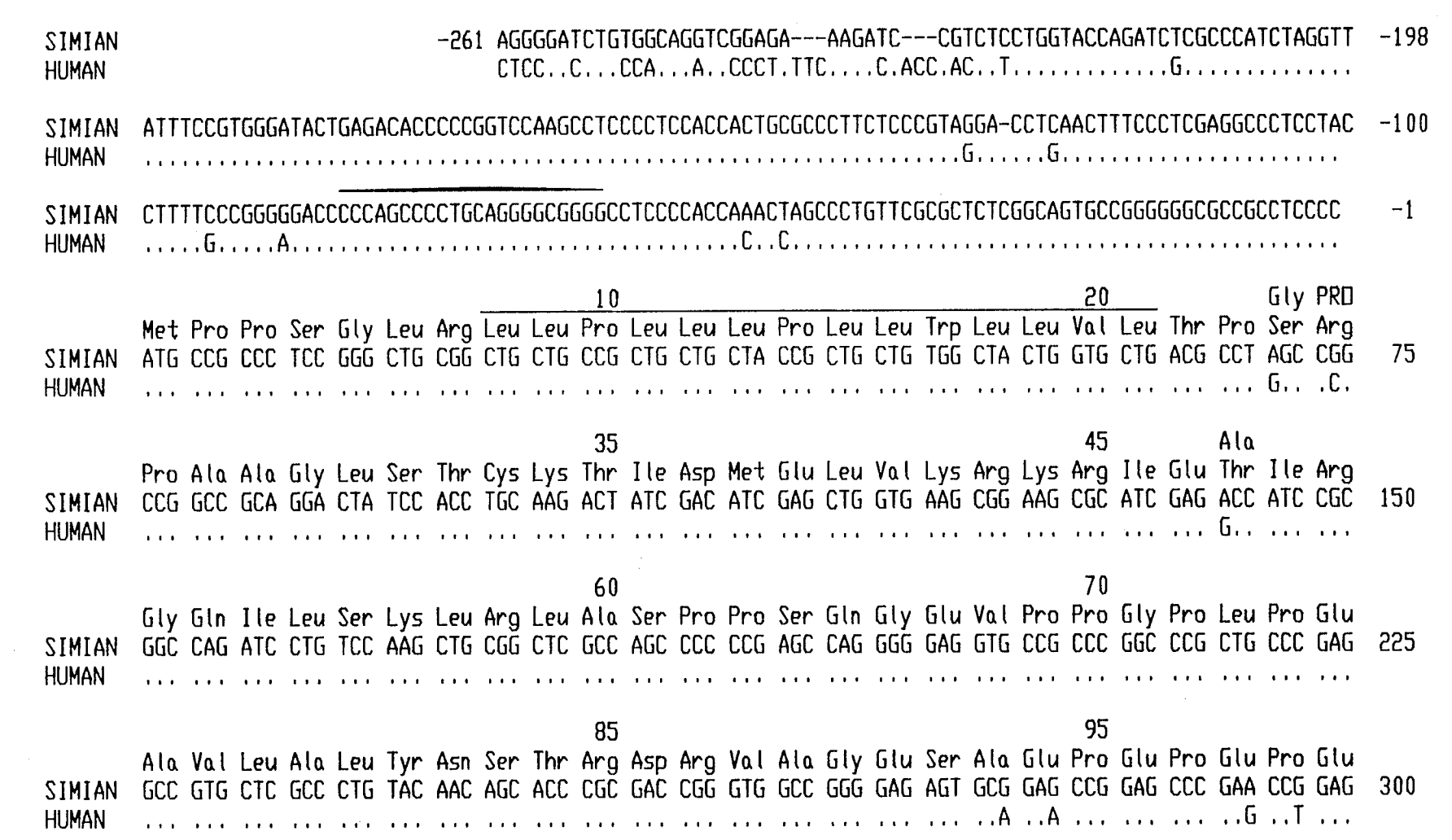
Figure 1B:
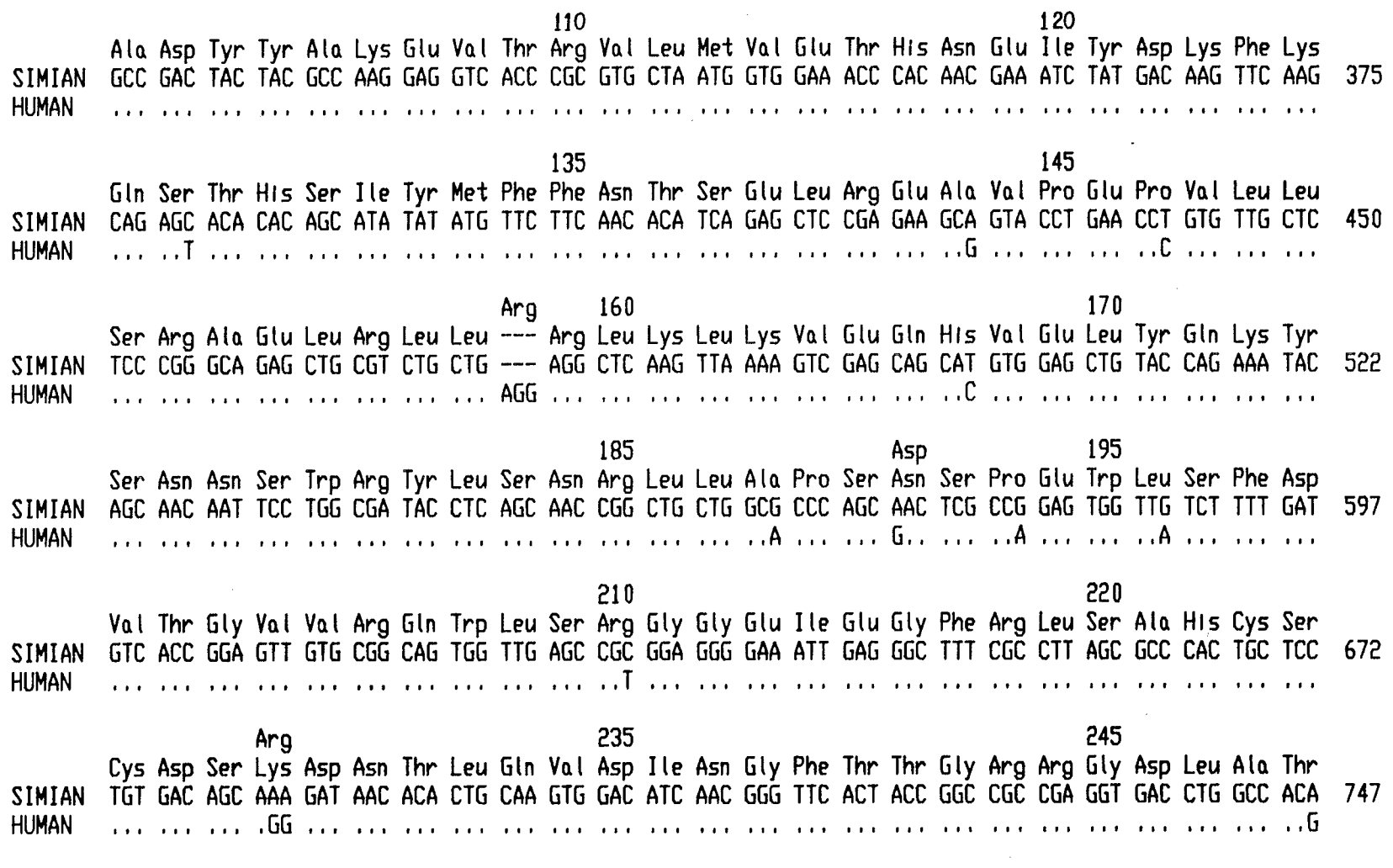

FIG. 1A, FIG. 1B and FIG. 1C depict in sequential order the nucleotide sequence of simian TGF-β1 cDNA and deduced amino acid sequence. The 1600 bp insert of pTGF-β1-2 was subcloned into the M13mp18 and M13mp19 cloning vectors (Yanisch-Perron et al., 1985, Gene 33:103–119) and both strands were sequenced using the dideoxy chain-termination method (Sanger et al., 1977, Proc. Natl. Acad. Sci. USA 74:5463–5467). The deduced amino acid sequence of simian TGF-β1 is presented directly above the cDNA sequence. The human TGF-β1 nucleotide sequence is aligned with and presented directly below the simian cDNA sequence; dots indicate homologous nucleotide residues within the sequences. Amino acid differences between the human and simian proteins are indicated in the top line. The mature TGF-β1 sequence is boxed and the signal peptide is overlined.

FIG. 2A, FIG. 2B, FIG. 2C, and FIG. 2D depict in sequential order the nucleotide sequence of human TGF-β2-442 cDNA and deduced amino acid sequence. The 2597 bp insert of PC-21 was subcloned into pEMBL (Dante et al., 1983, Nucleic Acids Res. 11:1645–1654) and sequenced on both strands using the dideoxy chain-termination method (Sanger et al., 1977, Proc. Natl. Acad. Sci. USA 74:5463–5467). The coding sequence is shown and the deduced amino acid sequence is presented directly above. The mature TGF-β2 sequence is boxed and the signal peptide is overlined. Potential glycosylation sites are indicated by asterisks. The arrow indicates the putative signal sequence cleavage site. The nucleotide sequence of simian TGF-β2-414 cDNA is identical to the human TGF-β2-442 cDNA sequence except that (a) nucleotides 346 through 432 (bracketed) are deleted and replaced by the sequence AAT, and (b) several silent nucleotide changes occur elsewhere in the structure (indicated by single letters directly below the changed nucleotide). The deduced amino acid sequence for simian TGF-β2-414 precursor is identical to the human TGF-β2-442 precursor amino acid sequence except that Asparagine replaces amino acid residues 116 through 144 in the human TGF-β2-442 structure. The nucleotide sequence of a human TGF-β2-414 cDNA has been sequenced through the region indicated by broken underlining and was found to be perfectly homologous to the human TGF-β2-442 cDNA sequence except that nucleotides 346 through 432 are deleted and replaced by the sequence AAT.

FIG. 3A, FIG. 3B, and FIG. 3C depict in sequential order the nucleotide sequence of hybrid TGF-β1/β2 precursor DNA and deduced amino acid sequence. The coding sequence is shown and the deduced amino acid sequence is presented directly above. The mature TGF-β2 sequence is boxed and the precursor signal peptide is overlined. Glycosylation sites are indicated by asterisks. The arrow indicates the putative signal sequence cleavage site. The TGF-β2 mature coding sequence depicted is of human origin. The simian TGF-β2 mature coding sequence is nearly identical to the human sequence: only 3 silent base changes occur and are indicated by single letters directly below the changed nucleotide.

5. DETAILED DESCRIPTION OF THE INVENTION

The present invention is directed to a method for inhibiting HIV infection and/or replication using TGF-β. The invention is based upon the discovery that both mature and precursor forms of TGF-β1 and TGF-β2 are effective in inhibiting HIV induced syncytia formation and production of virus in infected host cells in vitro. TGF-β used in accordance with the invention may be obtained from natural sources, by genetic engineering, or chemical synthetic techniques such as those described herein. Indeed, hybrid TGF-β1/β2 compounds can be constructed utilizing recombinant DNA or chemical synthetic techniques.

While the applicants are under no duty or obligation to explain the mechanism by which the invention works, it may be that TGF-β gains entry into infected CD4 positive cells which co-express the cellular receptor for TGF-β. Entry of TGF-β may involve one receptor for the mature form and a different or additional receptor for the precursor molecule. This is described more fully in the subsections below.

Once inside the infected cells, TGF-β may function at any of a number of levels including but not limited to alteration of the cell cycle, DNA replication, viral transcription, translation and/or post-translational events that inhibit HIV replication. Regardless of the mechanism by which TGF-β works to inhibit HIV, any TGF-β molecule chosen can be tested in the in vitro assay system described herein in order to assess its inhibitory activity and dose.

5.1 TGF-β: MATURE AND PRECURSOR FORMS

In accordance with the invention, the mature or precursor form of TGF-β1 or TGF-β2 or TGF-β1/β2 molecules may be used to inhibit HIV. These will all be referred to herein generically as TGF-β. In theory, any of these molecules should bind to and enter infected cells which also express the receptor for the mature form of TGF-β. However, it is possible that the TGF-β precursor may gain entry into infected cells via a different cellular receptor.

Results presented in copending application Ser. No. 189,894 filed May 3, 1988, now abandoned, which is incorporated by reference herein in its entirety, suggests that the TGF-β1 precursor which is normally processed intracellularly to elaborate the mature molecule, may itself have biological activity and specificity for cell receptors which recognize mannose-6-phosphate residues of glycoproteins.

The processing scheme proposed for the maturation of TGF-β from the precursor, while not complete, emphasizes several of the steps which have been at least partially defined. Although the order of the various processing steps has not been characterized completely, they are described as occurring in succession to facilitate comprehension. The first step involves signal peptide cleavage at the Gly-29/Leu-30 peptide bond. This cleavage event most likely occurs co-translationally during transit of the precursor through the rough endoplasmic reticulum membrane (Blobel and Dobberstein, 1975, J. Cell. Biol. 67:835–851; Walter et al., 1984, Cell 38:5–8). Following cleavage of the signal peptide, core glycosylation units (Rothman et al., 1978, Cell 15:1447–1454) are added at each of the predicted N-glycosylation sites located at Asn-82, Asn-136 and Asn-176. The core glycosylated molecule is then sequentially processed during transit through the golgi to yield a phosphorylated glycoprotein, containing complex, sialylated oligosaccharides. At some stage during synthesis or transit, proteolytic cleavage at the dibasic residue and disulfide isomerization occurs, releasing mature TGF-β1.

The presence of mannose-6-phosphate in the TGF-β1 precursor is detected and raises the possibility that the precursor possesses an independent function. Mannose-6-phosphate, a phosphorylated sugar analog, appears to play a fundamental role in the targeted transport and intercellular exchange of lysosomal enzymes (von Figura, 1986, Ann. Rev. Biochem 55:167–193). Specific receptors which recognize the mannose-6-phosphate residues of lysosomal enzymes have been identified and are essential components of the transport system. Secreted lysosomal proteins containing mannose-6-phosphate have been identified in the conditioned medium of tissue culture cells (Gal and Gottesman, 1986, J. Biol. Chem. 261:1760–1765; Capony et al., 1981, J. Cell. Biol. 104:253–262; Baumbach et al., 1984, Proc. Natl. Acad. Sci. USA 81:2985–2989; Sahagian and Gottesman, 1982, J. Biol. Chem. 257:11145–11150). All of these proteins, however, exhibit acid hydrolase activity. The mannose-6-phosphate residues of the TGF-β1 precursor may direct the molecule to lysomes for proteolytic processing to yield mature TGF-β1. Alternatively, the mannose-6-phosphate residues may function to target the cleavage TGF-β1 precursor to lysosomes for degradation.

It has recently been reported that the cation-independent mannose-6-phosphate receptor is identical to the insulin-like growth factor II (IGF-II) receptor (Morgan et al., 1987, Nature 329:301–307; Roth et al., 1987, Biochem. Biophys. Res. Comm. 149:600–606; MacDonald, 1988, Science 239:1134–1137). This receptor appears to be bifunctional, containing separate binding sites for IGF-II and mannose-6-phosphate. Although the biological significance of a single receptor which binds IGF-II and proteins containing mannose-6-phosphate is unclear, this bifunctional receptor may play important roles for signal transduction and/or for targeted sorting of receptor bound proteins. Proliferin, a prolactin-related glycoprotein, thought to be an autocrine growth regulator (Lee and Nathens, 1987, Endocrinology 120:208–213), has been shown to contain mannose-6-phosphate and to bind tightly to IGF-II/-mannose-6-phosphate receptors (Lee and Nathens, 1988, J. Biol. Chem. 263:3521–3527). It is possible that the TGF-β1 precursor interacts specifically with this bifunctional or other mannose-6-phosphate cell surface receptor. Thus, it may be that the TGF-β1 precursor can gain entry into cells that lack the receptor for the mature form of the molecule. As a result, it may be beneficial to use the precursor to treat HIV infected cells that do not express the receptor for mature TGF-β.

5.2. SOURCES OF TGF-β

In accordance with the invention, the TGF-β used to inhibit HIV infection may be obtained from a variety of sources. These include but are not limited to isolating natural TGF-β from appropriate sources, production of TGF-β by recombinant DNA techniques, production of TGF-β by chemical synthetic methods etc.

5.2.1. TGF-β1

TGF-β1, a disulfide linked homodimer (9 cysteine residues per chain) contains two identical subunits (112 amino acid residues per subunit) and utilizes a receptor distinct from either TGF-alpha or EGF (Frolik et al., 1984, J. Biol. Chem. 160:10995–11000; Tucker et al., 1984, Proc. Natl. Acad. Sci. USA 81:6757–6761).

Natural TGF-β1 can be isolated from a variety of sources. This potent modulator of cell behavior is synthesized by a variety of normal and transformed cells in culture (Roberts et al., 1981, Proc. Natl. Acad. Sci. USA 78:5339–5343) and has been purified from various sources including placenta (Frolik et al., 1983, Proc. Natl. Acad. Sci. USA 80:3676–3680), kidney (Roberts et al., 1983, Biochemistry 22:5692–5698), urine (Twardzik et al., 1985, J. Cell. Biochem. 28:289–297) and blood platelets (Childs et al., 1982, Proc. Natl. Acad. Sci. USA 79:5312–5316). Additionally, the human (Derynck et al., 1985, Nature 316:701–705), mouse (Derynck et al., 1986, J. Biol. Chem. 261:4377–4379), and simian (Sharples et al., 1987, DNA 6:239–244) TGF-β1 have been described.

Large quantities of TGF-β1 may be obtained by recombinant DNA techniques using eucaryotic host cells transfected with recombinant DNA vectors containing the TGF-β1 coding sequence controlled by expression regulatory elements. Examples of such methods are described in copending application Ser. No. 189,894 filed May 3, 1988, now abandoned, a continuation-in-part of application Ser. No. 147,842 filed Jan. 25, 1988, now abandoned, a continuation-in-part of application Ser. No. 055,662 filed May 29, 1987, now abandoned, each of which is incorporated by reference herein in its entirety. Briefly, a cDNA clone coding for simian TGF-β1 precursor was obtained from a cDNA library made from an African Green Monkey cell line, BSC-40. The deduced amino acid sequence of the mature simian TGF-β1 shown boxed in FIG. 1C has 100% homology with that of the mature human TGF-β1. Strong sequence homology was found between the precursor regions of the human and simian proteins with only five amino acid changes out of 278 residues.

The simian (and murine) precursor sequence was found to code for one less amino acid residue than the human.

Expression vectors were constructed which contain the entire coding sequence for the simian TGF-β1 placed under the control of SV40 expression elements. They were used to transfect Chinese Hamster Ovary cells (CHO cells). The resulting CHO transfectants produce and secrete both mature recombinant TGF-β1 which has a biological activity comparable to authentic TGF-β1, as well as the precursor form of recombinant TGF-β1 which also has a biological activity.

5.2.2. TGF-β2

Natural TGF-β2 used in accordance with the invention can be obtained from a variety of sources. A protein isolated from bovine demineralized bone has been identified as being related to TGF-β (Seyedin et al., 1987, J. Biol. Chem. 262:1946–1949). The protein has also been isolated from porcine platelets (Cheifetz et al., 1987, Cell 48:409–415), a human prostatic adenocarcinoma cell line PC-3 (Ikeda et al., 1987, Biochemistry 26:2406–2410), and a human glioblastoma cell line (Wrann et al., 1987, EMBO 6:1633–1636). Partial amino acid sequence of this protein indicated that it was homologous to TGF-β and has been termed TGF-β2.

Large quantities of TGF-β2 may be obtained by recombinant DNA techniques using eukaryotic host cells transfected with recombinant DNA vectors containing a TGF-β2 coding sequence controlled by expression regulatory elements. Examples of such methods are described in copending application Ser. No. 234,065 filed Aug. 18, 1988, now abandoned, a continuation-in-part of application Ser. No. 148,267 filed Jan. 25, 1988, now abandoned, a continuation-in-part of Ser. No. 106,752 filed Oct. 6, 1987, now abandoned, each of which is incorporated by reference herein in its entirety. Briefly, cDNA clones coding for human TGF-β2 precursor were obtained from a cDNA library made from a tamoxifen treated human prostatic adenocarcinoma cell line, PC-3. The cDNA sequence of one such clone is shown in FIGS. 2A–2D and predicts that TGF-β2 is synthesized as a 442 amino acid polypeptide precursor from which the mature 112 amino acid TGF-β2 subunit is derived by proteolytic cleavage. This TGF-β2 precursor, termed TGF-β2-442, shares a 41% homology with the precursor of TGF-β1. In another embodiment, cDNA clones coding for simian TGF-β2 precursor were obtained from a cDNA library made from an African green monkey kidney cell line, BCS-40. The cDNA sequence of one such clone predicts that TGF-β2 is also synthesized as a 414 amino acid polypeptide precursor from which the mature 112 amino acid TGF-β2 subunit is derived by proteolytic cleavage. This TGF-β2 precursor, termed TGF-β2-414, has an amino acid sequence of 414 amino acid residues and is identical to the amino acid sequence of TGF-β2-442, except that it contains a single Asparagine residue instead of the 29 amino acid sequence from residue numbers 116 to 135 of the human TGF-β2-442 sequence.

Clones from the BSC-40 cDNA library which encode a simian TGF-β2-442 precursor as well as clones from the human PC-3 cDNA library which encode a human TGF-β2-414 precursor have also been identified. The human and simian TGF-β2-442 precursors appear to be perfectly homologous at the amino acid level, as do the human and simian TGF-β2-414 precursors.

The mature 112 amino acid monomers of TGF-β1 and TGF-β2 show 71% homology.

5.2.3 HYBRID TGF-β1/β2

Hybrid TGF-β1/β2 molecules can be prepared using recombinant DNA techniques or synthetic methods. Examples of such methods are also described in copending applications Ser. No. 234,065, filed Aug. 18, 1988, now abandoned, and Ser. No. 189,894 filed May 3, 1988, now abandoned, each of which is incorporated by reference herein in its entirety. Briefly, expression vectors containing the TGF-β2 mature coding sequence joined in-phase (i.e., in the same translational reading frame) to the TGF-β1 signal, and precursor sequences (see FIG. 3A–3C) were constructed and used to transfect Chinese Hamster Ovary cells (CHO cells). The resulting CHO transfectants produce and secrete mature, biologically active TGF-β2.

5.2.4. MODIFIED TGF-β

Variations in the amino acid sequences shown herein for the different TGF-β molecules, as well as variations in the steric configuration, the type of covalent bonds which link the amino acid residues, and/or addition of groups to the amino- or carboxy-terminal residues are within the scope of the invention. For example, the TGF-β molecule used in accordance with the invention may include altered sequences such as conservative alterations which result in a silent change thus producing a functionally equivalent molecule. Thus, the amino acid sequences shown in FIGS. 1-3 may be altered by various changes such as insertions, deletions and substitutions, either conservative or non-conservative, where such changes might provide for certain advantages in their use. As used herein, conservative substitutions would involve the substitution of one or more amino acids within the sequences shown with another amino acid having similar polarity and hydrophobicity/hydrophilicity characteristics resulting in a silent alteration and a functionally equivalent molecule. Such conservative substitutions include but are not limited to substitutions within the following groups of amino acids: glycine, alanine; valine, isoleucine, leucine; aspartic acid, glutamic acid; asparagine, glutamine; serine, threonine; lysine, arginine; phenylalanine, tyrosine; and methionine, norleucine.

Additional amino acids or other chemical groups may be added to either the amino or carboxy terminus of TGF-β in order to alter or enhance its activity. For example, the addition of hydrophobic groups may increase the permeability of the TGF-β molecule and enhance its entry into the infected cells.

In another embodiment of the invention, TGF-β may be linked to a carrier molecule. For example, TGF-β could be covalently coupled to an antibody molecule specific for CD4 positive cells, HIV-infected cells, or some other cell surface antigen that will allow the TGF-β to be targeted to cells which express that particular antigen. In this way, the TGF-β molecule could be altered so that it is taken up by infected cells that may not express a receptor for the particular type of TGF-β molecule chosen for use. Such coupling techniques are well known in the art and can include but are not limited to the use of crosslinking agents, schiff-base formation, amide bonds, peptide bonds, sulfide bonds, etc.

5.3. IN VITRO ASSAY FOR DEMONSTRATING HIV INHIBITORY EFFECT OF TGF-β

The inhibitory activity of the TGF-β compositions can be measured and the functional equivalency and/or increased efficacy of altered TGF-β molecules can readily be tested using an in vitro assay system such as any of those described in Section 6 et seq. herein. For example, the efficacy of any TGF-β composition selected may be assessed by its relative ability to inhibit (a) the formation of syncytia, and (b) the production of HIV particles in HIV-infected cells in vitro using a target cell line that can be infected with HIV. In general such cell lines would be of a T-cell or myelocytic/-monocytic lineage or another cell type transfected with the gene for CD4. Alternatively, where the TGF-β is linked to a "targeting" molecule e.g., a monoclonal antibody, hormone, growth factor etc. the target cell line should express the appropriate cell surface antigen or receptor for the molecule conjugated to TGF-β.

In order to assess the efficacy of the TGF-β molecule chosen, the target cell should be grown in vitro, infected with HIV and treated with different doses of the TGF-β before, during or after infection (e.g., limited dilution techniques can be used). The inhibitory effect on virion production may be assessed as described, e.g., by measuring (a) production of HIV by assaying for HIV proteins, such as the p24 core protein or reverse transcriptase, in the culture media; (b) the induction of HIV antigens in cells by immunofluorescence; or (c) the reduction in syncytia formation assessed visually. The ability of TGF-β or altered TGF-β molecules to inhibit HIV is indicative of the inhibitory activity and inhibitory dose of the TGF-β compound tested.

5.4. USES OF HIV INHIBITORY TGF-β

The TGF-β composition may be used in accordance with the invention in vivo to prevent the formation of syncytia and the production of HIV virions and, thus, inhibit the progression of HIV infection within an exposed patient. Effective doses of TGF-β formulated in suitable pharmacological carriers may be administered by any appropriate route including but not limited to injection (e.g., intravenous, intraperitoneal, intramuscular, subcutaneous, etc.), by absorption through epithelial or mucocutaneous linings (e.g., oral mucosa, rectal and vaginal epithelial linings, nasopharyngeal mucosa, intestinal mucosa, etc.); etc.

In addition, TGF-β may be mixed in any suitable pharmacological carrier, linked to a carrier or targeting molecule (e.g., antibody, hormone, growth factor, etc.) and/or incorporated into liposomes, microcapsules, and controlled release preparations prior to administration in vivo.

In another embodiment, TGF-β may be used in conjunction with other treatments for HIV infection. For example, TGF-β may be used in conjunction with antiviral compounds that inhibit reverse transcriptase activity (e.g., AZT); with soluble CD4 or monoclonal antibodies that inhibit HIV absorption to cells; or with other cytokines and growth factors (e.g., interferon α, β or γ; tumor necrosis factor, interleukin-2, granulocytic/monocytic colony stimulating factor; colony stimulating factor-1, etc.); and with agents that are used to treat other microorganisms or viruses that opportunistically infect AIDS patients.

In another embodiment of the invention, TGF-β can be used in vitro to test the efficacy of different drugs. In this regard, it would be advantageous to obtain bone marrow samples from an AIDS patient and expose the marrow in vitro to the drug, compound or regimen being tested in order to identify those that, for example, kill the virus yet spare normal cells, or those that will stimulate marrow repopulation. However, bone marrow derived from AIDS patients exhibits very poor marrow colony formation in vitro. This is probably due to infection of the precursor CD4+ cells with HIV. As a result, the efficacy of various drugs tested in vitro is difficult or impossible to assess. The use of TGF-β to inhibit HIV in such an assay system should increase marrow colony formation in vitro and therefore, permit the screening of various other protocols and drugs on the marrow activity in vitro.

6. EXAMPLE INHIBITION OF HIV INFECTION USING TGF-β

The experiments described below demonstrate the inhibitory effect of TGF-β1 and TGF-β2 on HIV infection of target cells of T-cell origin in culture in vitro. The mature and precursor forms of TGF-β1 and mature TGF-β2 were most effective against HIV.

6 1. MATERIALS AND METHODS

6.1.1. CELLS AND VIRUS

CEM-F cells were originally derived from the acute human lympyhoblastic leukemia and represent an established T lymphoblastoid line. They are available at the American Type Culture Collection as CCRF-CEM cells (ATCC No. CCL 119).

The $LAV_{BRU}$ strain of human immune deficiency virus (HIV) was obtained from Dr. Luc Montagnier, Institut Pasteur, Paris, France. The virus was adapted to CEM-F cells, and stored in small aliquots in liquid nitrogen. The titer of the virus was determined every two to three weeks and is expressed as $TCID_{50}$ (tissue culture inhibitory doses; i.e., the amount of virus necessary to reduce the viral expression by 50%). In all experiments described in the subsections below, a viral dose of 30 $TCID_{50}$ was used.

Both the CEM-F cells and the HIV virus were grown in LAV/CEM medium. The medium consists of RPMI 1640, supplemented with 1% glutamine, 100 U/ml of Penicillin, 100 μg/ml Streptomycin, 2 μg/ml Polybrene, and 10% fetal bovine serum.

6.1.2. TGF-β PREPARATIONS

The following TGF-β preparations were used in the examples that follow: Natural mature TGF-β1 (nTGF-β1) was isolated from bovine spleen. TGF-β mature and precursor forms were also produced by recombinant DNA techniques described in copending applications defined in Sections 5.2.1, and 5.2.2 above (rTGF-β1 mature and rTGF-β1 precursor). One preparation contained a mature rTGF-β1 molecule lacking 17 to 18 amino acid residues possibly located at the amino terminus of the mature molecule (rTGF-β1 amino-less mature) as determined by Western blot analysis and amino acid composition. Natural mature TGF-β2 (nTGF-β2) derived from PC-3 cells was also used.

6.1.3. DETERMINATION OF THE PROLIFERATIVE EFFECT OF TGF-β

For each assay $2\times10^4$ CEM-F cells/well were plated in 96 well plates. The cells were mixed with each different factor preparation, each set up in quadruplicate. The total volume/well was 250 μl. Plates were incubated for six days at 37° C. and 5% $CO_2$. On day six, cells were labeled for four hours with 1 μCi/well of $^3$HTdR (New England Nuclear Corp. specific activity 6.7 Ci/mmol) harvested onto glass fiber filters and counted in the scintillation counter (Hartzman, R. J., Segall, M., Bach, M. L., and Bach, F. H., 1971, Histocompatibility matching. VI. Miniaturization of the mixed leukocyte culture test: A preliminary report. Transplantation, 11:268-273). The results were expressed as percent $^3$HTdR uptake of the control which consisted of cells incubated without factors. In addition, the results can be expressed as a tissue culture toxic dose 50 ($TCTD_{50}$), which represents the amount in μg of the factor necessary to reduce the number of cells by 50% as compared to the control.

6.1.4. INHIBITION OF HIV REPLICATION

The CEM-F cells were plated in 96 well plates at $2 \times 10^4$ cells/well and mixed with $30TCID_{50}$ of virus for 45 minutes. After 45 minutes the factors were added to each well and incubated as described for the proliferation assay. At the end of day six the supernatants were tested for the presence of viral antigen using an antigen capture ELISA assay described below. The assay uses two monoclonal antibodies against the viral core protein p24gag (Hu, S. H. et al., 1987, Nature 328:721-723; and Kinney Thomas, E. et al., 1988, AIDS 2:25-29).

6.1.5. ANTIGEN-CAPTURE ASSAY

For this assay Microtiter plates (96 well plates) were coated with two monoclonal antibodies: 25-2 (ATCC #9407) and 25-3 (ATCC #9408), each diluted at 1:2500. These antibodies (capture reagents) are specific for p24, p40, and p55 HIV gag proteins. Horseradish peroxidase (HRP)-conjugated human IgG purified from a serum of a seropositive individual was used as a signal. The absorbance (450/630 nm) is determined after the addition of substrate - tetramethyl benzidine (TMB). The OD readings fall into three categories: Experimentals=values from wells containing cells, viral inoculum and factor; and Controls=values from wells containing cells and virus (100%); and Background=values from wells containing viral inoculum alone. The background value was subtracted from all the OD values. The antiviral effect of the factors is expressed as the percent p24gag binding of the control. For example, if that value is 20%, it means that the viral replication, measured indirectly through p25gag binding, is inhibited by 80%.

6.1.6. SYNCYTIA FORMATION

Prior to collecting supernatants for the antigen-capture assay, all the wells were visually examined. This was done to assure that the infection took place and also to check the state of the cells. The syncytia were easy to observe, and although they were not counted, the differences in their numbers between wells were very apparent.

6.2. ANALYSIS OF TOXICITY OF TGF-β

The toxicity of TGF-β was tested against the host cell CEM-F (ATCC CCL119). CEM-F is a T-cell line that constitutively expresses the CD4 receptor, and therefore, is an appropriate host cell target for HIV infection. The effect of TGF-β on proliferation of uninfected cells was assessed by measuring thymidine incorporation in uninfected CEM-F cells treated with rTGF-β1 mature; rTGF-β1 precursor; rTGF-β1 amino-less mature; and nTGF-β2 as described in Materials and Methods above. The results of such experiments are shown in Table I below.

TABLE I

| PROLIFERATION OF CEM-F CELLS IN PRESENCE OF TGF-β1 | | |
|---|---|---|
| | $^3$H-TdR Incorporation in Uninfected CEM-F Cells[a] | |
| TGF-β (125 ng/well) | (cpm) | (% Control) |
| rTGF-β1 mature | 156,350 ± 7,317 | 84 |
| rTGF-β1 precursor | 165,337 ± 4,084 | 88 |
| rTGF-β1 amino-less mature | 149,022 ± 16,094 | 80 |
| nTGF-β2 (125 ng/well) | 172,802 ± 8,934 | 92 |
| None | 186,909 ± 47,421 | 100 |

[a]CEM-F cells were seeded into 96-well plates and treated with the TGF-β preparation indicated. Control wells were not treated. After 6 days $^3$H-TdR was added, and incorporation into cells was measured (cpm) 4 hours after treatment. Each cpm (except the control) reflects the mean of 4 samples. The control CPM represents the mean of 16 samples.

The results shown in Table I indicate none of the TGF-β preparations tested were toxic to CEM-F cells.

6.3. HIV INHIBITION BY TGF-β

In order to assess the effect of TGF-β on HIV infection, CEM-F cells were infected with HIV and treated with the following TGF-β preparations as described in Materials and Methods above: rTGF-β1 mature; rTGF-β1 precursor; rTGF-β1-amino-less mature; and nTGF-β2. Controls were infected with HIV, but not treated with TGF-β. The degree of infection was measured in two ways: (a) scoring HIV-induced syncytia formation in the wells at the end of the assay; and (b) measuring p24 in the spent culture medium using a monoclonal antibody specific for p24 in an ELISA format. Results of these experiments, described in more detail in Materials and Methods above, are shown in Table II below.

TABLE II

| INHIBITORY EFFECT OF TGF-β1 ON HIV | | | |
|---|---|---|---|
| | Inhibition of HIV in CEM-F Cells[a] | | |
| | ELISA p24 | | |
| TGF-β (15.5 ng/well) | (O.D.) | (% Infected Control) | Cytopathic Effect (Syncytia Formation) (+ wells/total wells) |
| rTGF-β/mature | 0.219 | 21 | + |
| rTGF-β/precursor | 0.363 | 35 | ± |
| rTGF-β1-amino-less mature | 0.817 | 78 | ++++ |
| nTGF-β2 | 0.143 | 14 | + |
| Untreated | 1.048 | 100 | ++++ |

[a]$2 \times 10^4$ CEM-F cells/well were seeded into 96-well plates and infected with HIV at $30TCID_{50}$ per well and treated with TGF-β as indicated. At 6 days post-inoculation, wells were visually examined and scored for syncytia formation. Supernatants from the culture wells were removed and added to 96-well ELISA plates precoated with MAb 25-2 + 25-3 which define p24 of HIV. ELISAs were performed and the optical density (O.D.) read at wavelengths of 450/630 nm. Results reflect the mean of 4 samples, except for the control that is a mean of 34 samples. O.D.s were compared to those of untreated infected controls and are also expressed as percentages.

The results shown in Table II indicate that mature TGF-β1, precursor TGF-β1 and mature TGF-β2 had an inhibitory effect on HIV-infection; however, the TGF-β2 amino-less mature had little or no effect. These results indicate that the amino terminus of the mature TGF-β molecule may be important for its activity.

7. EFFECTS OF TGF-β TREATMENT ON HIV INFECTIVITY IN A HUMAN MONOCYTE/MACROPHAGE CELL LINE

The monocyte/macrophage may serve as a major reservoir of HIV infection in vivo. Therefore, the monocyte/macrophage is an important target cell to include in the evaluation of potential HIV anti-infectives. We used the promonocyte cell line, U937, to address this issue to compare the susceptibility of untreated U937 cells and cells treated with TGF-β to infection with HIV-1.

7.1. MATERIALS AND METHODS

U937 cells were pre-incubated in media containing rTGF-β1 mature (at 2 and 20 ng/ml), rTGF-β1 precursor (at 6 and ng/ml), or media alone for eight hours prior to virus infection. The medium is exactly the same as that used in the assays described in Section 6 above. $2.5 \times 10^4$ pretreated cells/well were added to the appropriate wells of a 96-well micro-titer plate.

A virus dilution plate was prepared containing virus at 1000, 100, 50, 25, 12, 6, 3, and 0 TCID$_{50}$/well. The calculation of the TCID$_{50}$ of the virus stock was based on prior infectivity titrations with the virus stock. The cells were inoculated and incubated overnight at 37° C. The inoculum was removed and the cells refed with media containing the appropriate factor and were incubated at 37° C.

On days 3, 5, and 7 post-infection, supernatants were removed for the HIV p24 antigen capture assay described in Section 6 above. Cells were refed with media containing the appropriate factor and incubated at 37° C. On day 8 post-infection, cells were removed for the immunofluorescence assay. Results are shown in Table III.

TABLE III

EFFECTS OF TGF-β ON HIV INFECTIVITY IN A HUMAN MONOCYTE/MACROPHAGE CELL LINE

| HIV Virus Input (TCID$_{50}$) | Number of Wells Positive for Virus Expression* | | |
|---|---|---|---|
| | Media Control | rTGF-β mature (2-20 ng/ml) | rTGF-β precursor (6-60 ng/ml) |
| 1000 | 8/8 | 8/8 | 8/8 |
| 100 | 8/8 | 6/8 | 7/8 |
| 50 | 8/8 | 4/8 | 5/8 |
| 25 | 8/8 | 2/8 | 4/8 |
| 12 | 8/8 | 5/8 | 4/8 |
| 6 | 1/8 | 2/8 | 3/8 |
| 3 | 0/8 | 0/8 | 0/8 |
| 0 | 0/8 | 0/8 | 0/8 |

*Virus expression was measured by two methods:
1. Extracellular viral core protein was measured on day 7 using the p24 antigen capture assay on culture supernatants.
2. Intracellular viral protein expression was measured on day 8 with an immunofluorescence assay on acetone-fixed cells.
The wells demonstrated a one-to-one correspondence between the two assays, (i.e., if the supernatant p24 assay was negative, then the cells were negative for expression of HIV antigens by immunofluorescence).

The present invention is not to be limited in scope by the cell lines, TGF-β molecules and assays exemplified which are intended as but single illustrations of one aspect of the invention. Indeed, various modifications of the invention in addition to those shown and described herein will become apparent to those skilled in the art from the foregoing description and accompanying figures. Such modifications are intended to fall within the scope of the appended claims.

What is claimed is:

1. An vitro method for inhibiting HIV in a cell infected with HIV comprising contacting said cell with transforming growth factor-β in an amount effective for inhibiting HIV infection or replication.

2. The method according to claim 1 in which the transforming growth factor-β comprises a mature TGF-β1.

3. The method according to claim 1 in which the transforming growth factor-β comprises a TGF-β1 precursor.

4. The method according to claim 1 in which the transforming growth factor-β comprises a mature TGF-β2.

5. The method according to claim 1 in which the transforming growth factor-β comprises a TGF-β2 precursor.

6. The method according to claim 1 in which the transforming growth factor-β comprises a TGF-β1/β2 hybrid precursor.

* * * * *